United States Patent [19]

Yoshida et al.

[11] Patent Number: 5,246,949
[45] Date of Patent: Sep. 21, 1993

[54] PREPARATION FOR ENDERMISM CONTAINING DOPAMINE DERIVATIVES

[75] Inventors: Mitsuhiro Yoshida; Hiroyuki Fujimori; Yoshio Ishino, all of Saitama; Akira Sasaki, Tokyo; Masayoshi Kasai, Gifu; Keiji Ohmori, Gunma; Noriko Konita, Saitama; Yoshifumi Yuasa; Toyohiko Kobayashi, both of Tokyo, all of Japan

[73] Assignees: Sansho Co., Ltd.; Takasago International Corp., both of Tokyo, Japan

[21] Appl. No.: 908,890

[22] Filed: Jul. 8, 1992

Related U.S. Application Data

[63] Continuation of Ser. No. 623,831, Dec. 6, 1990, abandoned.

[30] Foreign Application Priority Data

Dec. 6, 1989 [JP] Japan .................................. 1-317343
Jun. 20, 1990 [JP] Japan .................................. 2-161845

[51] Int. Cl.$^5$ .................... A61K 31/44; A61K 31/225
[52] U.S. Cl. .................................... 514/356; 514/249; 514/357; 514/406; 514/427; 514/548; 514/947
[58] Field of Search ............... 514/356, 357, 249, 548, 514/427, 406, 947

[56] References Cited

U.S. PATENT DOCUMENTS

| | | | |
|---|---|---|---|
| 4,218,470 | 8/1980 | Casagrande et al. | 424/311 |
| 4,302,471 | 11/1981 | Casagrande et al. | 424/311 |
| 4,581,225 | 4/1986 | Su et al. | 424/45 |
| 4,637,930 | 1/1987 | Konno et al. | 424/28 |
| 4,764,379 | 8/1988 | Sanders et al. | 424/449 |
| 4,832,954 | 5/1989 | Sato et al. | 424/449 |

FOREIGN PATENT DOCUMENTS

| | | |
|---|---|---|
| 0279986 | 8/1988 | European Pat. Off. |
| 0321870 | 6/1989 | European Pat. Off. |
| 2141025 | 12/1984 | United Kingdom |
| 2142237 | 1/1985 | United Kingdom |

OTHER PUBLICATIONS

Chemical Abstracts 87:29044z (1977).
F. Azzollini et al; *International Journal of Clinical Pharmacology, Therapy and Toxicology;* 26(2), pp. 105–112; (1988).
Nichols et al; *The Journal of Pharmacology and Experimental Therapeutics;* 242(2); pp. 573–578; (1987).
Julian M. Henwood et al; *Drugs;* 36; pp. 11–31; (1988).
C. Casagrande et al; *Arzneim.-Forsch./Drug Res.;* 36(1); pp. 291–303; (1986).
F. Pocchiari et al; *Arzneim.-Forsch./Drug Res.;* 36(1); pp. 334–340; (1986).
A. Salvadeo et al; *International Journal of Clinical Pharmacology, Therapy and Toxicology;* 26(2); pp. 98–104; (1988).
E. Lodola et al; *Arzneim.-Forsch./Drug Res.;* 36(1); pp. 345–348; (1986).
Sol I. Rajfer et al; *Circulation;* 73; pp. 740–748; (1986).
M. Okumura et al; *Chem. Pharm. Bull.;* 37(5); pp. 1375–1378; (1989).

*Primary Examiner*—Leonard Schenkman
*Attorney, Agent, or Firm*—Sughrue, Mion, Zinn, Macpeak & Seas

[57] ABSTRACT

(A) a diacylated dopamine derivative represented by the formula (I):

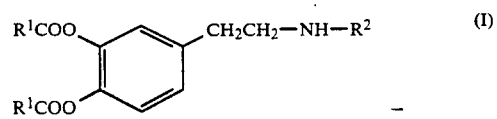

wherein $R^1$ represents an alkyl group having 3 to 7 carbon atoms, a cycloalkyl group having 3 to 6 carbon atoms, substituted or unsubstituted phenyl group or a substituted or unsubstituted nitrogen-containing heterocyclic group; and $R^2$ represents a hydrogen atom or a lower alkyl group; or a salt thereof; and (B) one or more compounds selected from lactic acid esters, fatty acid monoglycerides and higher alcohols; optionally together with (C) an unsaturated fatty acid monohydric alcohol ester. This preparation has a sustained effect, a high skin permeability and a low skin irritativeness.

7 Claims, 6 Drawing Sheets

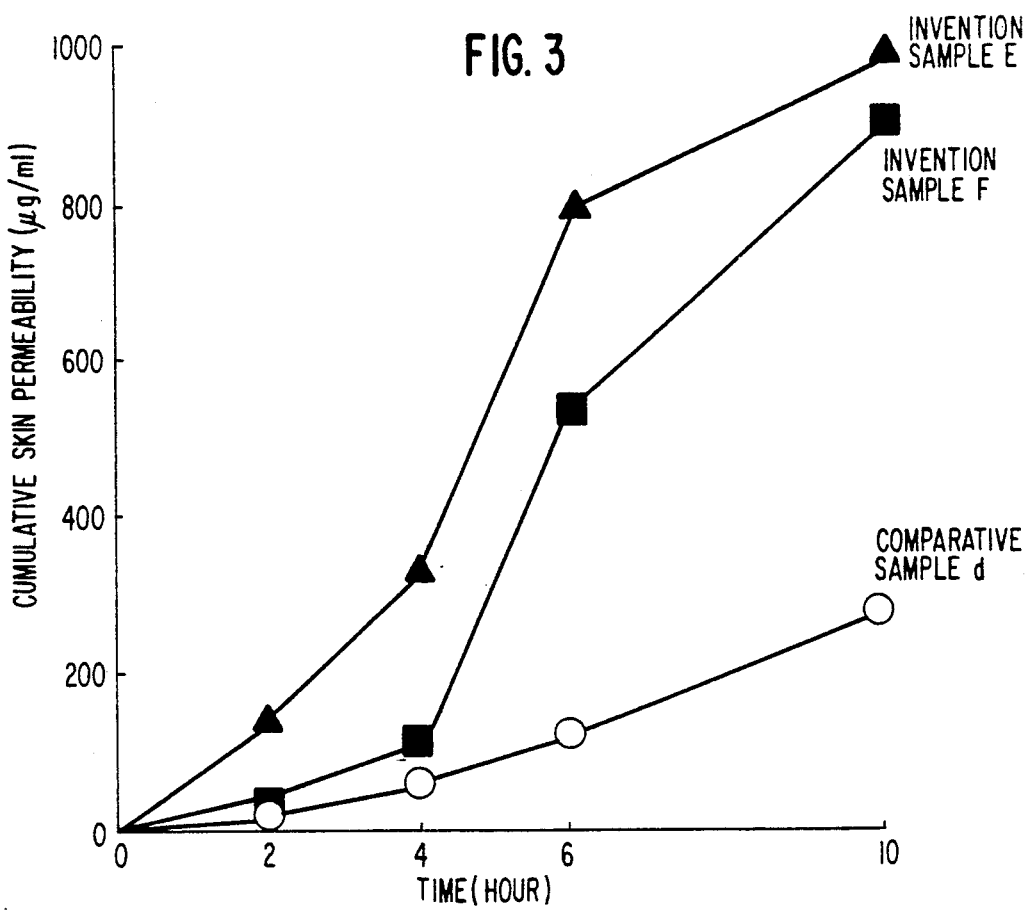
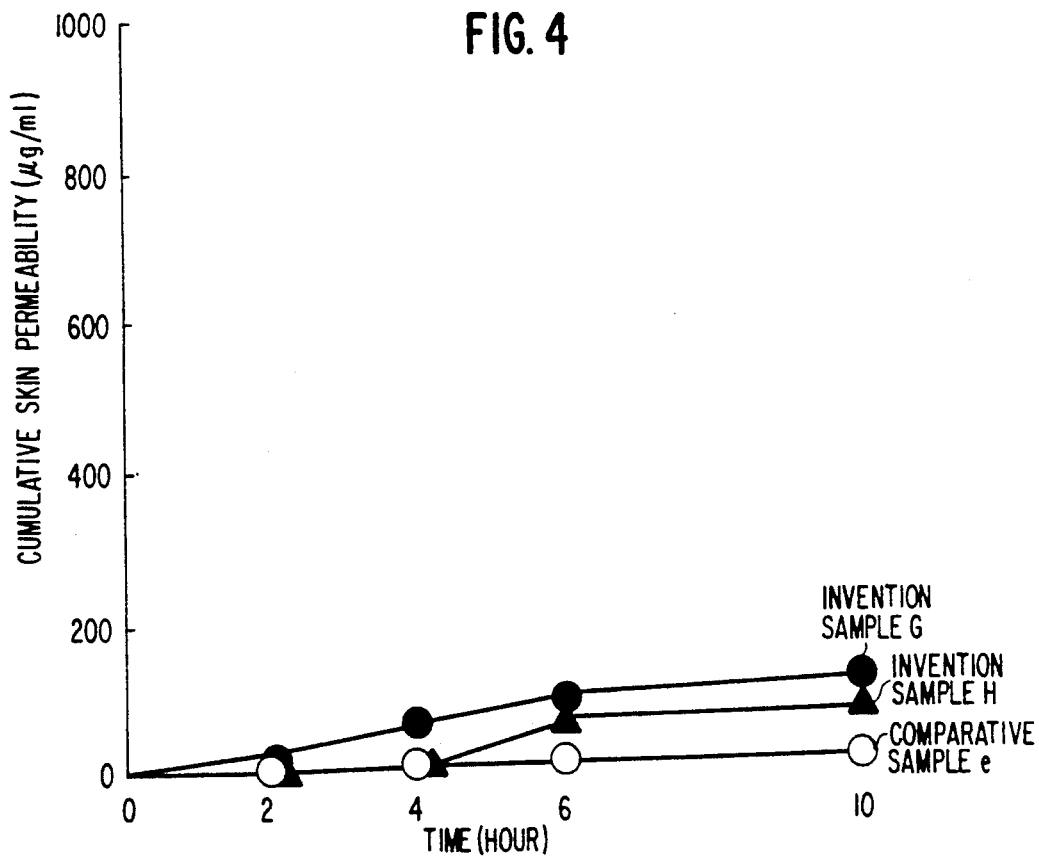

PREPARATION FOR ENDERMISM CONTAINING DOPAMINE DERIVATIVES

This is a continuation of application Ser. No. 07/623,831, filed Dec. 6, 1990, abandoned.

FIELD OF THE INVENTION

This invention relates to a preparation for endermism containing a dopamine derivative. More particularly, it relates to a preparation for endermism containing dopamine derivative which shows a high skin permeability and a low skin irritativeness.

BACKGROUND OF THE INVENTION

Dopamine, which is represented by formula (II):

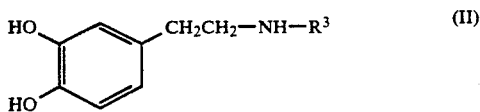

wherein $R^3$ is a hydrogen atom; and dobutamine, which is represented by the above formula (II) wherein $R^3$ is a group,

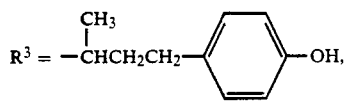

have been used for the treatment of, for example, hypotension, cardiac circulatory insufficiency and cardinogenic shock. However, since each of these compounds has a free catechol group and is scarcely absorbed when administered orally or percutaneously, the administration of them is restricted to the continuous intravenous way.

Recently, ibopamine represented by formula (III):

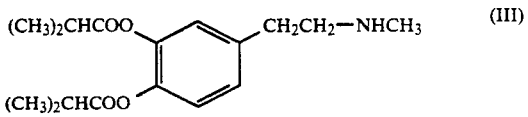

has been developed as a drug which exerts a dopamine-like effect and can be orally administered (cf. U.S. Pat. Nos. 4,218,470 and 4,302,471). However this compound is still unsatisfactory in sustained effect and it is reported that the half-life of this compound in plasma is 1.54 hour [cf. E. Lodola et al; Arzneim.-Forsch./Drug Res., 36(1), 345–348 (1986)]. It is further reported that the effect of ibopamine on improvement of the circulation, when evaluated by the cardiac coefficient, sustains 3 to 6 hours [cf. SOL I. Rajifer et al.; Circulation, 73, 740–748 (1986)].

Recently, further attempts have been made to develop a preparation capable of gradually releasing a drug in the blood for a prolonged period of time so as to improve the persistence of the effect of the drug. For example, U.S. Pat. No. 4,581,225 discloses a sustained release nasal preparation which comprises a catechol amine (for example, dobutamine), an emulsifier, a dispersant and an agent rendering the drug slowly released such as oleic acid, linolic acid or an ester thereof. Further, Okumura et al. have studied on the application of dopamine hydrochloride to the skin and reported that the use of a 5% aqueous solution of glyceryl monocaprylate can elevate the percutaneous penetration rate of dopamine hydrochloride to a level 34 times as high as that achieved by using dopamine hydrochloride alone [cf. Chem. Pharm Bull., 37(5), 1375–1378 (1989)]. In the practical clinical application, however, it is preferable to establish a higher skin permeability. There is an additional problem, furthermore, that dopamine hydrochloride is highly irritative to the skin and causes skin damage if it can be percutaneously absorbed. Therefore, this compound is unsuitable for practical application.

Other known dopamine derivatives, which might exert the dopamine- like effects, include those synthesized by introducing variuos substituents into the catechol and/or amino group [cf. C. Casagrande et al.; Arzneim.-Forsch./Drug Res., 36(2), 291–303 (1986)].

SUMMARY OF THE INVENTION

An object of the present invention is to provide a preparation for endermism, having the dopamine-like effects, which is expected to be prolonged for a long period of time, a high skin permeability and a low skin irritativeness. As a result of extensive studies, the present inventors have found that the use of lactic acid esters, fatty acid monoglycerides or higher alcohols in combination with a dopamine derivative represented by the following formula (I) remarkably promotes the percutaneous absorption of said compound; and that the use of an unsaturated fatty acid monohydric alcohol ester remarkably reduces the skin irritativeness of said compound.

Accordingly, the present invention provides a preparation for endermism which comprises the following ingredients (A) and (B):

(A) a diacylated dopamine derivative represented by formula (I):

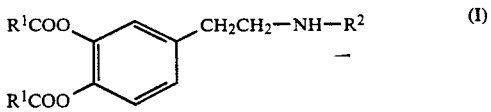

wherein $R^1$ represents an alkyl group having 3 to 7 carbon atoms, a cycloalkyl group having 3 to 6 carbon atoms, a substituted or unsubstituted phenyl group or a substituted or unsubstituted nitrogen-containing heterocyclic group; and $R^2$ represents a hydrogen atom or a lower alkyl group; or a salt thereof; and (B) one or more compounds selected from lactic acid esters, fatty acid monoglycerides and higher alcohols.

The present invention further provides a preparation for endermism which comprises the above ingredients (A) and (B), and the following ingredient (C):

(C) an unsaturated fatty acid monohydric alcohol ester.

BRIEF DESCRIPTION OF THE DRAWINGS

FIGS. 1 to 8 each show the results of the determination of the accumulated amount of the drug permeated through skin with the lapse of time of test samples in the in vitro skin permeation tests performed in Test Examples 1 to 8.

DETAILED DESCRIPTION OF THE INVENTION

Figure 1:
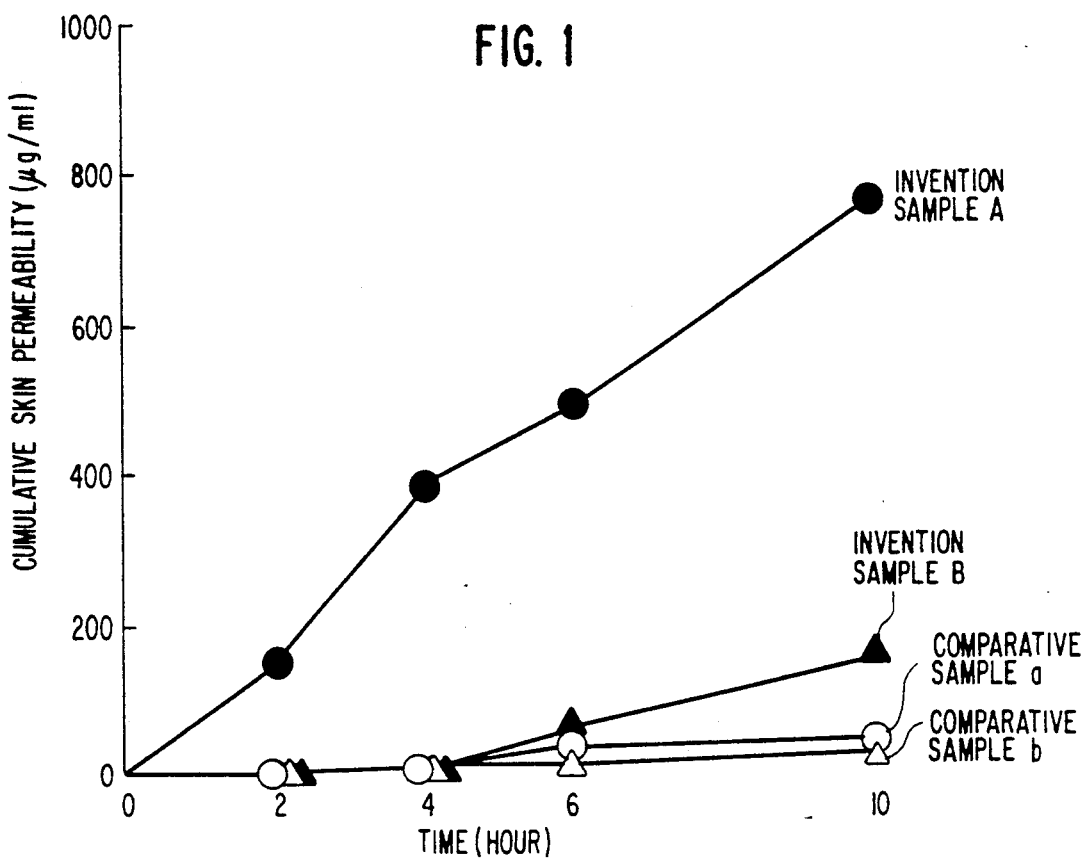

In formula (I), $R^1$ simultaneously represents the same group. Examples of the diacylated derivative of dopamine or a salt thereof to be used in the present invention as the ingredient (A) include 3,4-di-O-n-butyryldopamine, 3,4-di-O-n-butyrylepinine (epinine means N-methyldopamine), 3,4-di-O-n-butyryl-N-ethyldopamine, 3,4-di-O -n-butyryl-N-n-propyldopamine, 3,4-di-O-n-butyryl -N-isopropyldopamine, 3,4-di-O-isobutyryldopamine, 3,4-di-O -isobutyrylepinine, 3,4-di-O -isobutyryl-N-ethyldopamine, 3,4-di-O -isobutyryl-N-n-propyldopamine, 3,4-di-O-isobutyryl-N-isopropyldopamine, 3,4-di-O -pivaloyldopamine, 3,4-di-O-pivaloylepinine, 3,4-di-O-pivaloyl-N-ethyldopamine, 3,4-di-O-pivaloyl-N-n-propyldopamine, 3,4-di-O-pivaloyl-N-isopropyldopamine, 3,4-di-O-valeryldopamine, 3,4-di-O-valerylepinine, 3,4-di-O-valeryl-N-ethyldopamine, 3,4-di -O-valeryl-N-n-propyldopamine, 3,4-di O-valeryl-N-isopropyldopamine, 3,4-di-O-iscyaleryldopamine, 3,4-di-O-isovalerylepinine, 3,4-di-O -isovaleryl-N-ethyldopamine, 3,4-di-O -isovaleryl-N-n-propyldopamine, 3,4-di-O -isovaleryl-N-isopropyldopamine, 3,4-di-O -caproyldopamine, 3,4-di-O-caproylepinine, 3,4-di-O-caproyl-N-ethyldopamine, 3,4-di-O-caproyl-N-n-propyldopamine, 3,4-di-O -caproyl-N-isopropyldopamine, 3,4-di-O-2', -ethylbutyryldopamine, 3,4-di-O-2', -ethylbutyrylepinine, 3,4-di-O -2'-ethylbutyryl-N-ethyldopamine, 3,4-di-O-2'-ethylbutyryl,-N-n-propyldopamine, 3,4-di-O-2'-ethylbutyryl-N-isopropyldopamine, 3,4-di-O-2',2'-dimethylbutyryldopamine, 3,4-di-O-2',2'-dimethylbutyrylepinine, 3,4-di-O-2',2'-dimethylbutyryl-N-ethyldopamine, 3,4-di-O-2',2'-dimethylbutyryl-N-n-propyldopamine, 3,4-di-O-2',2'-dimethylbutyryl-N-isopropyldopamine, 3,4-di-O-3',3'-dimethylbutyryldopamine, 3,4-di-O-3',3'-dimethylbutyrylepinine, 3,4-di-O-3',3'-dimethylbutyrl-N-ethyldopamine, 3,4-di-O-3',3'-dimethylbutyryl-N-n-propyldopamine, 3,4-di-O-3',3'-dimethylbutyryl-N-isopropyldopmine, 3,4di-O-heptanoyldopamine, 3,4-di-O -heptanoylepinine, 3,4-di-O-heptanoyl-N-ethyldopamine, 3,4-di-O-heptanoyl-N-n-propyldopamine, 3,4-di-O-heptanoyl-N-isopropyldopamine, 3,4-di O-cyclopropylcarboxyldopamine, 3,4-di-O-cyclopropylcarbonylepimine, 3,4-di-O-cyclopropylcarbonyl-N-ethyldopamine, 3,4-di-O-cyclopropylcarbonyl-N-n-propyldopamine, 3,4-di-O-cyclopropylcarbonyl-N-isopropyldopamine, 3,4-di-O-cyclobutylcarbonyldopamine, 3,4-di-O -cyclobutylcarbonylepimine, 3,4-di-O-cyclobutylcarbonyl, N-ethyldopamine, 3,4-di-O-cyclobutylcarbonyl -N-n-propyldopamine, 3,4-di-O-cyclobutylcarbonyl N-isopropyldopamine, 3,4-di-O-cyclopentylcarbonyldopamine, 3,4-di-O-cyclopentylcarbonylepimine, 3,4-di-O-cyclopentylcarbonyl-N-ethyldopamine, 3,4-di-O-cyclopentyl-carbonyl-N-n-propyldopamine, 3,4-di-O-cyclopentylcarbonyl-N-isoprpyldopamine, 3,4-di-O-cyclohexylcarbonyldopamine, 3,4-di-O-cyclohexylcarbonyl-epinine, 3,4-di-O-cyclohexylcarbonyl -N-ethyldopamine, 3,4-di-O-cyclohexylcarbonyl -N-n-propyldopamine, 3,4-di-O-cyclohexylcarbonyl-N -isopropyldopamine, 3,4-di-O-cyclohexyldopamine, 3,4-di-O-benzoylepinine, 3,4-di-O benzoyl-N ethyldopamine, 3,4-di-O-benzoyl-N-n propyldopamine, 3,4-di-O-benzoyl-N-isopropyldopamine, 3,4-di-O-4'-methylbenzoyl-N-ethyldopamine, 3,4-di-O-4'-methylbenzoyl-N-n-propyldopamine, 3,4-di-O-4'-methylbenzoyl-N-isopropyldopamine, 3,4-di-O-4'-methoxybenzoyldopamine, 3,4-di-O-4'-kethoxybenzoylepinine, 3,4-di-O -4'-methoxybenzoyl-N-ethyldopamine, 3,4-di-O -4'-methoxybenzoyl-N-n-propyldopamine, 3,4-di-O-4'-methoxybenzoyl-N -isopropyldopamine, 3,4-di-O-2'-pyrrolecarbonyldopamine, 3,4-di-O-2'-pyrrolecarbonylepimine, 3,4-di O-2'-pyrrolecarbonyl-N-ethyldopamine, 3,4-di-O-2'-pyrrolecarbonyl-N-n-propyldopamine, 3,4-di-O-2'-pyrrolecarbynl-N-isopropyl -dopamine, 3,4-di-O-4'-pyrrazolecarbonydopamine, 3,4-di-O-4'-pyrazolecarbonoylepinine, 3,4-di-O-4'-pyrazonoyl-N-ethyldopamine, 3,4-di-O-4'-pyrazolecarbonyl-N-n-propyldopamine, 3,4-di-O-4'-pyrazolecarbonyl-N-isopropyldopamine, 3,4-di-O-nicotinoyldopamine, 3,4-di-O-nicotinoylepinine, 3,4-di-O -nicotinoyl-N-ethyldopamine, 3,4-di-O-nicotinoyl-N-n-propyldopamine, 3,4-O-nicotinoyl-N-isopropyldopamine, 3,4-di-O-5'-bromonicotinoyldopamine, 3,4-di-O-5'-bromonicotinoylepinine, 3,4-di-O-5'-bromonicotinoyl-N-ethyldopamine, 3,4-di-O -5'-bromonicotinoyl-N-n-propyldopamine, 3,4-di-O -5,-bromonicotinoyl -N-isopropyldopamine, 3,4-di-O-2'-methylnicotinoyldopamine, 3,4-di-O-2'-methylnicotinoylepinine, 3,4-di-O-2'-methylnicotinoyl-N-ethyldopamine, 3,4-di-O-2'-methylnicotinoyl-N-n-propyldopamine, 3,4-di-O-2'-methylnicotinoyl-N-isopropyldopamine, 3,4-di-O-6'-methylnicotinoyldopamine, 3,4-di-O-6'-methylnicotinoyl-epinine, 3,4-di-O-6'-methylnicotinoyl-N-ethyldopamine, 3,4-di-O-6'-methylnicotinoyl-N-n-propyldopamine, 3,4-di-O-6'-methylnicotinoyl-N-isopropyldopamine, 3,4-di-O-2'-pyrazinevcarbonyldopamine, 3,4-di-O-2'-pyrazinecarbonylepinine, 3,4-di-O-2'-pyrazinecarbonyl-N-ethyldopamine, 3,4-di-O-2'-pyrazinecarbonyl-N-n-propyldopamine, 3,4-di-O-2'-pyrazinecarbonyl-N-isopropyldopamine and nontoxic organic or inorganic acid salts thereof.

Examples of the organic acid salts include maleates, succinates and tartarates. Examples of the inorganic acid salts include hydrochlorides, hydrobromates, phosphates, nitrates and sulfates.

In formula (I), $R^1$ preferably represents a branched alkyl group or a pyridyl group and $R^2$ preferably represents a hydrogen atom and a methyl group. Among the compounds represented by formula (I) (hereinafter referred to as "Compound (I)"; the same expression shall apply to the other compounds), 3,4-di-O-isobutyryldopamine, 3,4-di-O-pivaloyldopamine, 3,4-di-O-isobutyrylepinine and 3,4-di-O-nicotinoyldopamine, and hydrochlorides thereof are particularly preferred.

These dopamine derivatives and salts thereof may be synthesized by known methods with the use of dopamine or epinine as a starting material [cf R. B. Walker et al.; J. Pharm. Sci., 67, 558 (1978), C. Casagrande et al.; Farmaco Ed. Sci., 28, 143 (1973) and C. Casagrande et al.; Arzneim.-Forsch./Drug Res., 36(2), 291–303 (1986)]. For example, 3,4-di-O -pivaloyldopamine represented by the following formula (I') may be synthesized in accordance with the following reaction scheme.

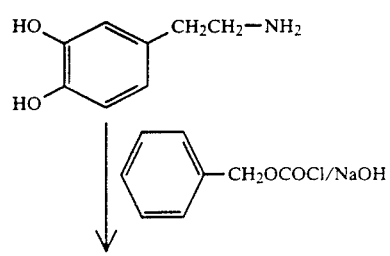

-continued

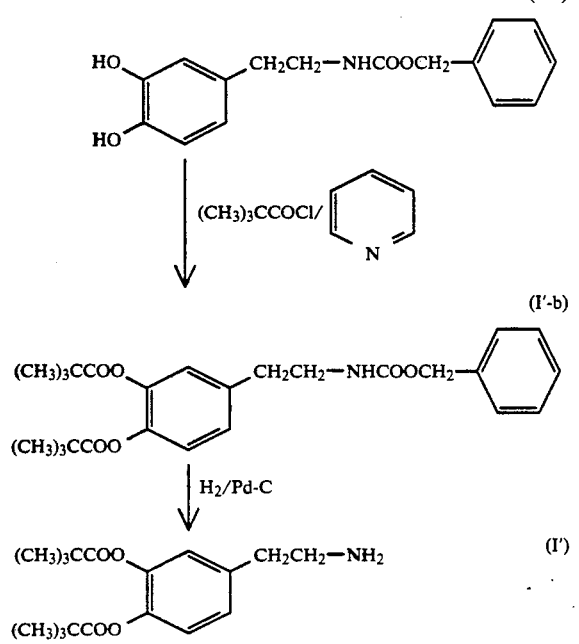

Namely, dopamine is reacted with benzyl chlorocarbonate in the presence of an alkali such as sodium hydroxide to protect the amino group. The intermediate (I'-a) thus obtained is then reacted with an acylating agent. Examples of the acylating agent include acyl anhydride, acyl chloride and acyl bromide. For example, pivaloyl chloride is reacted with the intermediate in pyridine to give a compound of the formula (I'-b). The compound (I'-b) is then subjected to catalytic reduction in methanol or acetic acid with the use of a metal catalyst (for example, palladium black, palladium carbon, Raney nickel, preferably palladium carbon) to give the desired compound (I'). Further, the thus-obtained compound (I') may be treated with an appropriate organic or inorganic acid selected from among those cited above and thus a corresponding salt thereof can be obtained.

The content of the dopamine derivative or a salt thereof, namely, the ingredient (A) in the preparation of the present invention ranges from 1 to 20% by weight, preferably 5 to 10% by weight, based on the weight of the preparation.

Examples of the lactic acid esters in the ingredient (B) to be used in the preparation of the present invention include myristyl lactate, cetyl lactate and lauryl lactate. Examples of the fatty acid monoglycerides include glyceryl monocaproate, glyceryl monocaprylate, glyceryl monocaprate, glyceryl mono-2-ethylhexanoate and glyceryl monolaurate. Among these compounds, glyceryl monocaprylate is particularly preferable. In the present invention, it is not preferable to use fatty acid diglycerides and fatty acid triglycerides, since these compounds hardly promote percutaneous absorption. Preferable examples of the higher alcohols include saturated or unsaturated alcohols having 12 to 18 carbon atoms such as lauryl alcohol, myristyl alcohol and oleyl alcohol.

As the ingredient (B), either one compound selected from lactic acid esters, fatty acid monoglycerides and higher alcohols or a mixture of two or more thereof may be employed. Preferably, lactic acid esters are used. In the preparation of the present invention, the proportion of the ingredient (B) contained in total to the dopanine derivative or a salt thereof ranges from 0.1 to 5, preferably 0.5 to 3, by weight.

The preparation of the present invention may further contain an unsaturated fatty acid monohydric alcohol ester, namely, the ingredient (C) in order to relieve the skin irritativeness. Examples of said unsaturated fatty acid monohydric alcohol ester include methyl linoleate, ethyl linoleate, propyl linoleate, methyl oleate, ethyl oleate and methyl linolenate. Among these compounds, methyl linoleate and ethyl linoleate are particularly preferable.

In the preparation of the present invention, the proportion of the unsaturated fatty acid monohydric alcohol ester, namely, the ingredient (C) to the dopamine derivative or a salt thereof ranges from 0.1 to 10, preferably 0.3 to 5, by weight.

The form of the preparation of the present invention is not particularly restricted. It may be formulated into, for example, an ointment, cream, gel, plaster or taping preparation.

In the preparation of the present invention, any base material may be used so long as it is commonly used in the preparations for endermism. Both oily base materials and aqueous base materials may be used therefor. Examples of the oily base materials include white vaseline, purified lanolin, squalane, silicone, liquid paraffin, vegetable oils and waxes. Examples of the aqueous base materials include water, lower alcohols, polyhydric alcohols and water soluble polymers. Furthermore, base materials commonly employed in plasters may be used therefor. Examples of these base materials include sticky materials such as natural rubber, synthetic rubber, styrene/isoprene/styrene copolymer (hereinafter referred to as SIS rubber), polyacrylate resins and polyisobutylene resins and polymer compositions such as soft polyamide resins, polyvinyl alcohol and polyacryl resins.

In addition to the above-described ingredients, the preparation of the present invention may further contain appropriate additives which are commonly employed in the preparations for endermism, for example, surfactants, stabilizers, preservatives ( e.g., methyl benzoate, ethyl benzoate and propyl benzoate), antiseptics (e.g., benzoic acid).

Usable as a substrate for a plaster or taping preparation are laminated films of polyethylene terephthalate and polyethylene vinyl alcohol.

The preparation of the present invention is applied onto the chest, the back or an arm of a patient usually once a day for treating, for example, hypotension or circulatory insufficiency.

The preparation for endermism of the present invention has the following characteristics which make it useful as a remedy for, for example, hypotension or cardiac circulatory insufficiency.
(1) It suffers from no first-pass effect in the liver and thus can be effectively utilized.
(2) It causes no damage on digestive tracts.
(3) It has a prolonged efficiency.
(4) It has little skin irritativeness.
(5) When any side effect (for example, hypersensitiveness such as eruption) is observed, the administration thereof can be immediately ceased, which means that it has a high safety.

The results of testing the skin permeability and skin irritativeness of the preparation of the present invention will be given with reference to the following test examples.

TEST EXAMPLES (1) in vitro skin permeability (i) Preparation of sample

Test on skin permeability upon the use of lactic acid esters [the ingredient (B)] or fatty acid monoglycerides [the ingredient (B)]

Comparative Samples 100 mg of each dopamine derivative hydrochloride as shown in Table 1 was weighed and 900 mg of propylene glycol was added thereto to obtain a solution or suspension containing 10% by weight of each dopamine derivative hydrochloride. These solutions and suspensions were referred to as comparative samples a to e, respectively.

Invention Samples 100 mg of each dopamine derivative hydrochloride as shown in Table 1 was weighed. Then 50 mg (in the cases of invention samples A to D) or 100 mg (in the cases of invention samples E to H) of each lactic acid ester or fatty acid monoglyceride as shown in Table 1 was added thereto. Further, propylene glycol was added to make the total amount 1000 mg. Thus, a solution or suspension containing 10% by weight of each dopamine derivative hydrochloride was obtained. These solutions and suspensions were referred to as invention samples A to H.

Test on skin permeability upon the use of higher alcohol [the ingredient (B) and test on skin permeability upon the combination use of higher alcohol [the ingredient (B)] and unsaturated fatty acid monohydric alcohol ester [the ingredient (C)]

Comparative Samples 100 mg of each dopamine derivative hydrochloride as shown in Table 2 was weighed and 900 mg of polyethylene glycol 400 was added thereto. Thus a solution or suspension containing 10% by weight of each dopamine derivative hydrochloride was obtained. These solutions and suspensions were referred to as comparative samples f to i respectively.

Invention Samples 100 mg of each dopamine derivative hydrochloride as shown in Table 2 was weighed and 100 mg of each higher alcohol as shown in Table 2 (in the cases of invention samples I, K, M and N) or 100 mg of each higher alcohol and 100 mg of each unsaturated fatty acid monohydric alcohol ester (in the cases of invention samples J and L) were added. Further polyethylene alcohol was added thereto to make the total amount 1000 mg. Thus, a solution or suspension containing 10% by weight of each dopamine derivative hydrochloride was prepared. These solutions and suspensions were referred to as invention samples I to N, respectively.

TABLE 2

| Test Ex. | Sample lot | Sample No. | Dopamine derivative | Higher alcohol | Unsaturated fatty acid monoglyceride alcohol ester |
|---|---|---|---|---|---|
| 5 | Comp. | f | 3,4-di-O-pivaloyldopamine hydrochloride | — | — |
|  | Invent. | I | 3,4-di-O-pivaloyldopamine hydrochloride | oleyl alcohol | — |
|  | Invent. | J | 3,4-di-O-pivaloyldopamine hydrochloride | oleyl alcohol | ethyl linoleate |
| 6 | Comp. | g | 3,4-di-O-isobutyryldopamine hydrochloride | — | — |
|  | Invent. | K | 3,4-di-O-isobutyryldopamine hydrochloride | myristyl alcohol | — |
|  | Invent. | L | 3,4-di-O-isobutyryldopamine hydrochloride | myristyl alcohol | ethyl oleate |
| 7 | Comp. | h | 3,4-di-O-isobutyrylepinine hydrochloride | — | — |
|  | Invent. | M | 3,4-di-O-isobutyrylepinine hydrochloride | lauryl alcohol | — |
| 8 | Comp. | i | 3,4-di-O-nicotinoyldopaimine hydrochloride | — | — |
|  | Invent. | N | 3,4-di-O-nicotinoyldopaimine hydrochloride | lauryl alcohol | — |

(ii) Test method

The abdominal hair of a male Wister rat, weighing 170 to 200 g and 7 weeks of age, was removed under anesthesia. After 24 hours, the animal was anesthetized

TABLE 1

| Test Ex. | Sample lot | Sample No. | Dopamine derivative | Lactic acid ester or fatty acid monoglyceride |
|---|---|---|---|---|
| 1 | Comp. | a | 3,4-di-O-pivaloyldopamine hydrochloride | — |
|  | Comp. | b | 3,4-di-O-isobutyryldopamine hydrochloride | — |
|  | Invent. | A | 3,4-di-O-pivaloyldopamine hydrochloride | myristyl lactate |
|  | Invent. | B | 3,4-di-O-isobutyryldopamine hydrochloride | cetyl lactate |
| 2 | Comp. | c | 3,4-di-O-isobutyrylepinine hydrochloride | — |
|  | Invent. | C | 3,4-di-O-isobutyrylepinine hydrochloride | myristyl lactate |
|  | Invent. | D | 3,4-di-O-isobutyrylepinine hydrochloride | glyceryl monocaprylate |
| 3 | Comp. | d | 3,4-di-O-nicotinoyldopaimne hydrochloride | — |
|  | Invent. | E | 3,4-di-O-nicotinoyldopaimne hydrochloride | lauryl lactate |
|  | Invent. | F | 3,4-di-O-nicotinoyldopaimne hydrochloride | glyceryl monocaprylate |
| 4 | Comp. | e | 3,4-di-O-butyryldopamine hydrochloride | — |
|  | Invent. | G | 3,4-di-O-butyryldopamine hydrochloride | cetyl lactate |
|  | Invent. | H | 3,4-di-O-butyryldopamine hydrochloride | glyceryl monocaprylate | and was confirmed to have no injury in the abdominal skin thereof. Next, the whole abdominal skin was cleansed with 70% ethanol and then peeled off under anesthesia.

The peeled skin was fixed on the lid of a horizontal membrane type in vitro diffusion cell (penetration area: 7.54 cm$^2$) in such a manner that the epidermis served as the donor face. As a receiver solution, 50 ml of physiological saline solution or a 30% aqueous solutioh of polyethylene glycol 400 was employed. On the donor side, 0.5 g of a solution of each sample was applied by adding dropwise. Then the lid was fixed in a receptor while paying attention so no bubbles remained in the derm side, followed by storing it in an incubator maintained at 32° C. The receptor solution was stirred with a stirrer and 0.5 ml portions thereof were collected with the lapse of time so as to determine the dopamine derivative contained therein. The determination was effected by high performance liquid chromatography. (iii) Test Results FIG. 1 shows the results of an in vitro test on skin permeability with the use of samples specified in the column of Test Example 1 in Table 1 (namely, comparative samples a and b and invention samples A and B).

As FIG. 1 clearly shows, the skin permeabilities of 3,4-di-O -pivaloyldopamine hydrochloride and 3,4-di -O-isobutyldopamine hydrochloride, which are dopamine derivatives obtained by acylating the catechol group of dopamine, were extremely elevated by adding a lactic acid ester.

Figure 2:
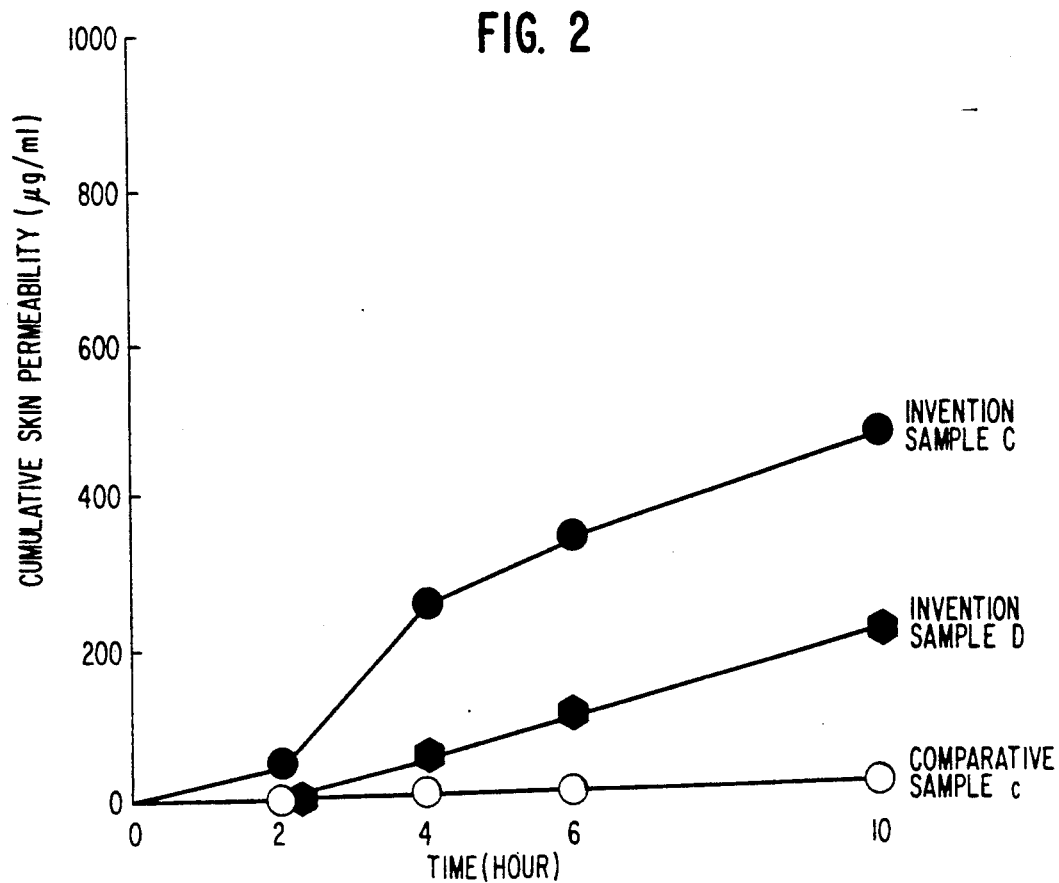
Figure 5:
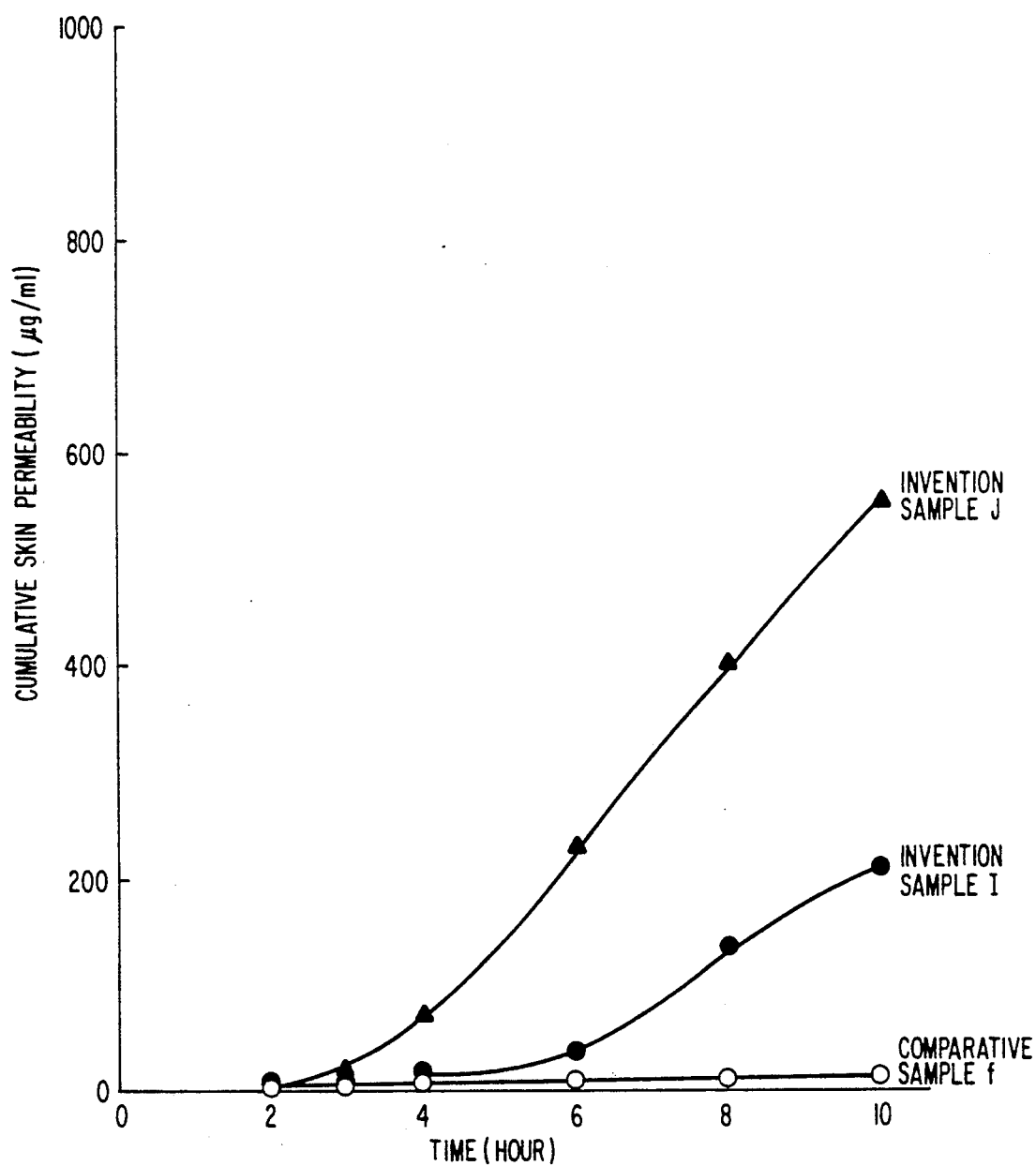
Figure 6:
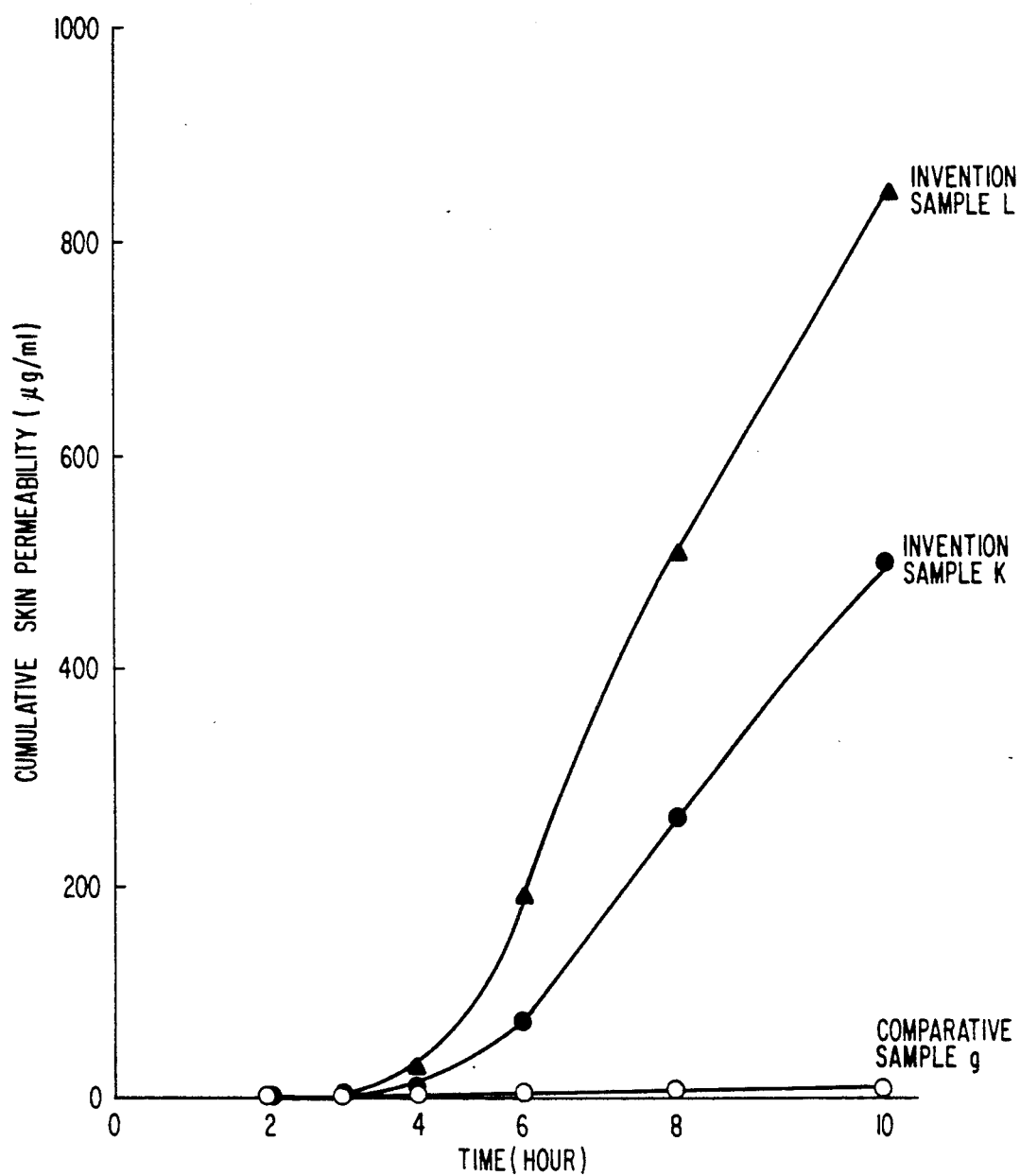
Figure 7:
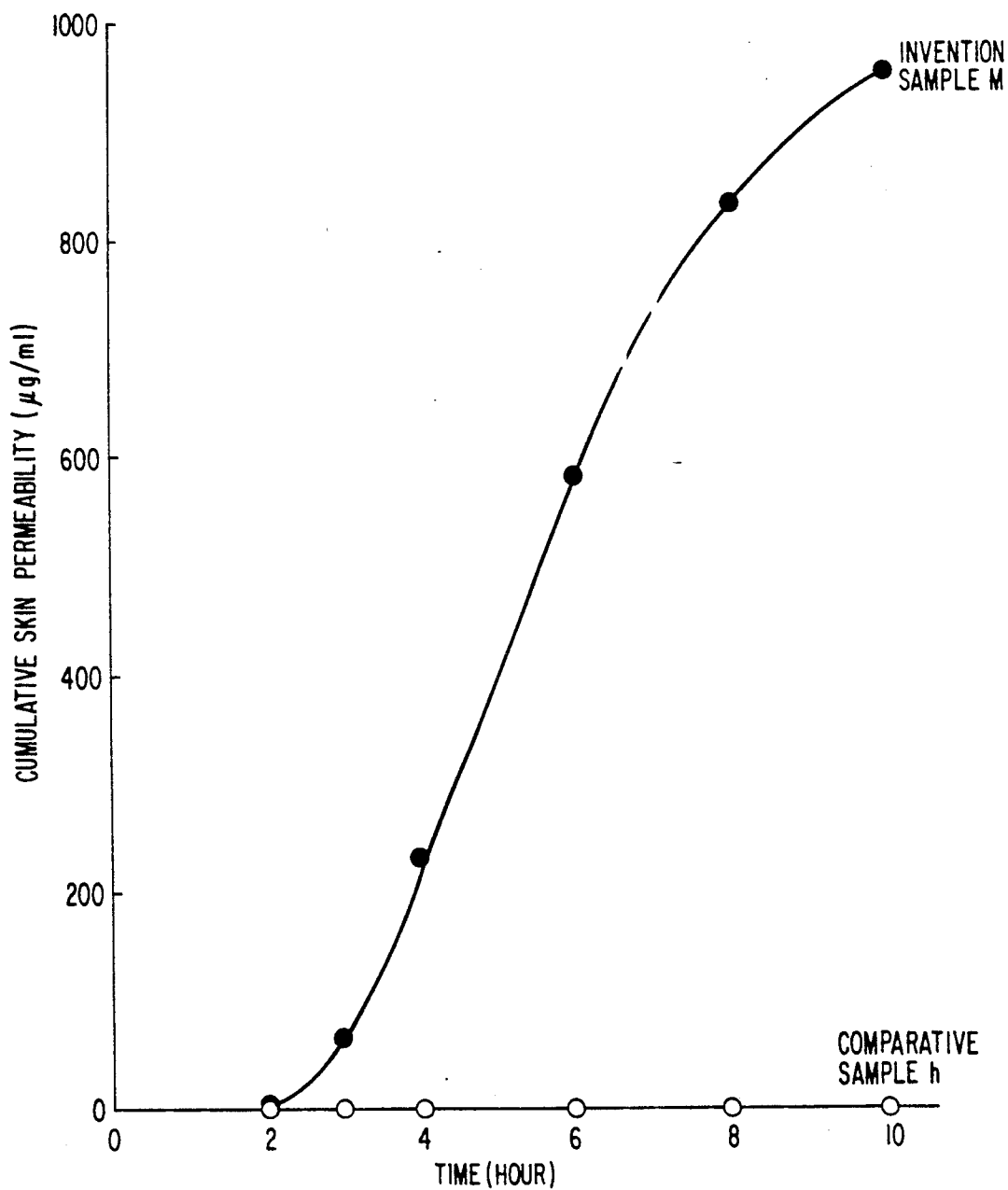
Figure 8:
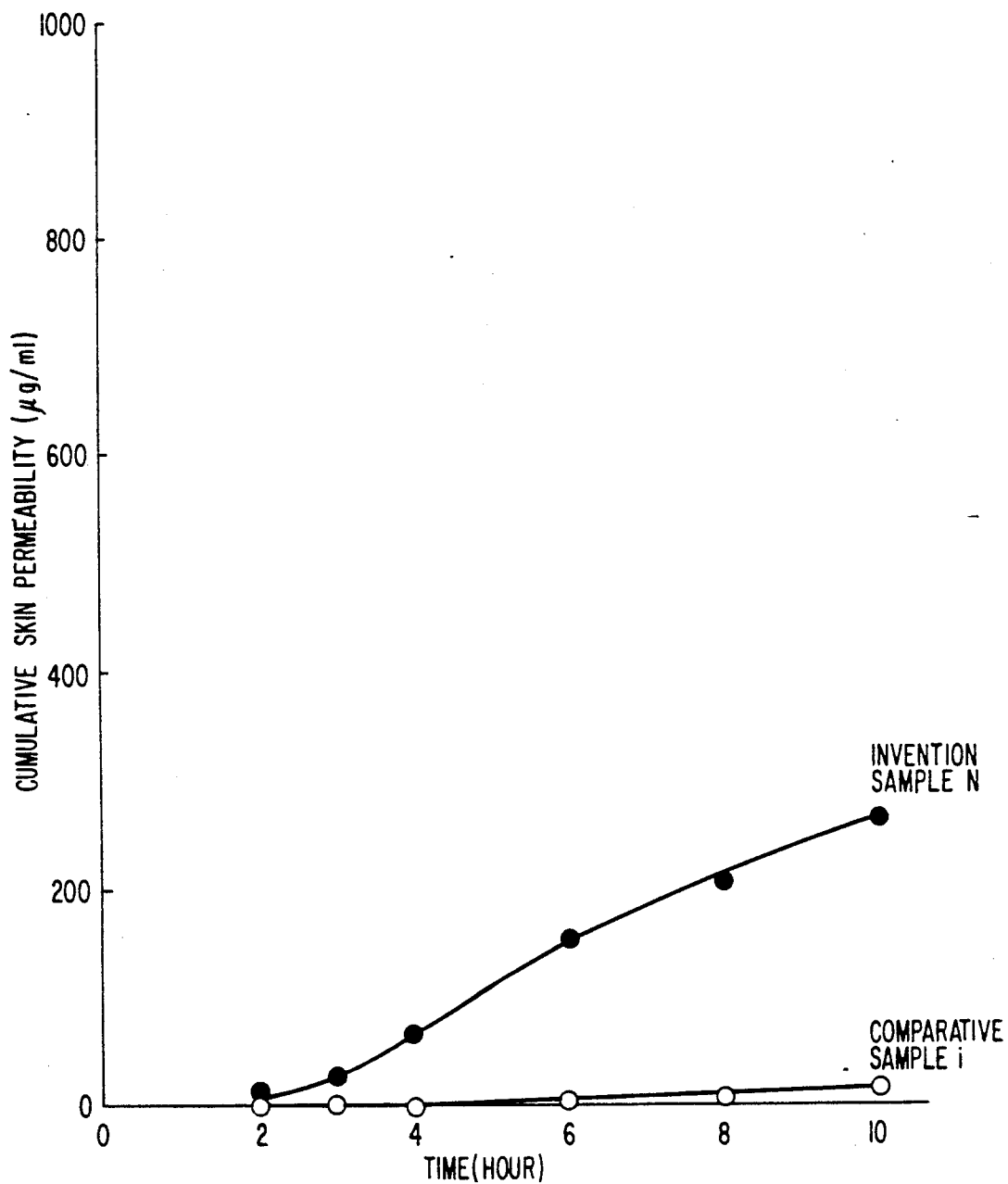

FIG. 2 shows the results of an in vitro test on skin permeability with the use of samples specified in the column of Test Example 2 in Table 1 (namely, comparative sample c and invention samples C and D).

As FIG. 2 clearly shows, the skin permeability of 3,4-di-O -isobutyrylepinine hydrochloride, which is a dopamine derivative obtained by acylating the catechol group of dopamine and substituting a hydrogen in the amino group in the side chain with a methyl group, was extremely elevated by adding a lactic acid ester or a fatty acid monoglyceride.

FIG. 3 shows the results of an in vitro test on skin permeability with the use of samples specified in the column of Test Example 3 in Table 1 (namely, comparative sample d and invention samples E and F).

As FIG. 3 clearly shows, the skin permeability of 3,4-di-O -nicotinoyldopamine hydrochloride, which is a dopamine derivative obtained by acylating the catechol group of dopamine, was extremely elevated by adding a lactic acid ester or a fatty acid monoglyceride.

FIG. 4 shows the results of an in vitro test on skin permeability with the use of samples specified in the column of Test Example 4 in Table 1 (namely, comparative sample e and invention samples G and H).

As FIG. 4 clearly shows, the skin permeability of 3,4-di-O -n-butyryldopamine hydrochloride, which is a dopamine derivative obtained by acylating the catechol group of dopamine, was extremely elevated by adding a lactic acid ester or a fatty acid monoglyceride. However, this compound was considerably decomposed after penetrating into the skin.

FIGS. 5 to 8 respectively show the results of in vitro tests on skin permeability with the use of samples specified in the columns of Test Examples 5 to 8 in Table 2 (namely, comparative samples f to i and invention samples I and N).

As FIGS. 5 to 8 clearly show, the skin permeabilities of 3,4-di-O -pivaloyldopamine hydrochloride, 3,4-di -O-isobutyldopamine hydrochloride, 3,4-di-O-isobutyrylepinine hydrochloride and 3,4-di-O-nicotinoyldopamine hydrochloride were extremely elevated by adding a higher alcohol.

In Test Examples 5 and 6, the invention samples J and L which were prepared by adding higher alcohols to the above-mentioned dopamine derivatives and further adding unsaturated fatty acid monohydric alcohol esters to the mixtures showed increased skin permeabilities compared with the cases wherein the higher alcohols alone were added.

(2) Test on primary skin irritativeness (i) Preparation of sample

Samples J and K 50 mg of dopamine hydrochloride or dobutamine hydrochloride as specified in Table 3 was weighed and 100 mg of propylene glycol and 850 mg of polyethylene glycol were added thereto to obtain a solution containing 5% by weight of dopamine or dobutamine. These preparation were referred to as samples j and k, respectively.

Samples O, Q, R, U and V 50 mg of each dopamine derivative hydrochloride as specified in Table 3 was weighed and 50 mg of a lactic acid ester or a fatty acid monoglyceride, as specified in Table 3, was added thereto. Further, 100 mg of propylene glycol and 800 mg of polyethylene glycol were added thereto to obtain a solution containing 5% by weight of each dopamine derivative hydrochloride. These solutions were referred to as samples O, Q, R, U and V, respectively.

Samples P, S, T, W and X 50 mg of each dopamine derivative hydrochloride as specified in Table 3 was weighed and 50 mg of a lactic acid ester or a fatty acid monoglyceride and 100 mg of an unsaturated fatty acid monohydric alcohol ester, as specified in Table 3, were added thereto. Further, 100 mg of propylene glycol and 700 mg of polyethylene glycol were added thereto to obtain a solution containing 5% by weight of each dopamine derivative hydrochloride. These solutions were referred to as samples P, S, T, W and X, respectively.

TABLE 3

| Test Ex. | Sample No. | Dopamine derivative | lactic acid ester or fatty acid monoglyceride | Unsaturated fatty acid monoglyceride alcohol ester |
|---|---|---|---|---|
| 9 | j | dopamine hydrochloride | — | — |
|  | k | dobutamine hydrochloride | — | — |
|  | O | 3,4-di-O-isobutyrylepinine hydrochloride | myristyl lactate | — |
|  | P | 3,4-di-O-isobutyrylepinine hydrochloride | myristyl lactate | ethyl linoleate |
| 10 | Q | 3,4-di-O-isobutyryldopamine hydrochloride | myristyl lactate | — |
|  | R | 3,4-di-O-pivaloyldopamine hydrochloride | glyceryl monocaprylate | — |
|  | S | 3,4-di-O-isobutyryldopamine hydrochloride | myristyl lactate | methyl linoleate |

TABLE 3-continued

| Test Ex. | Sample No. | Ingredient | | |
|---|---|---|---|---|
| | | Dopamine derivative | lactic acid ester or fatty acid monoglyceride | Unsaturated fatty acid monoglyceride alcohol ester |
| 11 | T | 3,4-di-O-pivaloyldopamine hydrochloride | glyceryl monocaprylate | ethyl linoleate |
| | U | 3,4-di-O-nicotinoyldopamine hydrochloride | myristyl lactate | — |
| | V | 3,4-di-O-n-butyryldopamine hydrochloride | cetyl lactate | — |
| | W | 3,4-di-O-nicotinoyldopamine hydrochloride | myristyl lactate | ethyl oleate |
| | X | 3,4-di-O-n-butyryldopamine hydrochloride | cetyl lactate | methyl oleate |

(ii) Test method

On the previous day of the test, the dorsal hair of a rabbit was removed. On the day of the test, 2 sites (2.5 cm ×2.5 cm) were located in the both sides of the median line, namely, 4 sites in total. The horny layers of epidermis of two of these sites were injured with an injection needle of 23G in such a manner as to form parallel crosses, while other two sites remained uninjured. 5 g of each sample prepared in the above-mentioned manner was applied onto doubled gauze pieces and this was then brought into contact with the injured and uninjured sites. Separately, two pairs of gauze pieces, to which a sample of the same composition as the one described above except that no dopamine derivative was contained had been applied, were brought into contact with the remaining skin of said animal. The back of the rabbit was coated with a linseed oil paper sheet and it was fixed with a tape. Further, it was covered with an elastic net so as to prevent the gauze from sliding. After 24 hours, the gauze pieces were removed and the skin was washed with warm water. Then the conditions of the skin were observed. The observation was repeated after 48 hours and thus the skin conditions were scored in accordance with Drays, skin reaction evaluation table (cf. Table 4). The scores of the uninjured and injured sites after 24 and 72 hours were totaled respectively and the average of each group, having 5 rabbits, was calculated. The obtained value was referred to as the primary skin irritation index.

TABLE 4

| | Skin reaction | Score |
|---|---|---|
| (1) | Formation of erythema and crusta: | |
| | No erythema | 0 |
| | Slight erythema | 1 |
| | Obvious erythema | 2 |
| | Moderate to serious erythema | 3 |
| | Serious erythema accompanied by crusta | 4 |
| (2) | Formation of edema: | |
| | No edema | 0 |
| | Slight edema | 1 |
| | Slight edema with obvious bosselation | 2 |
| | Moderate edema with bosselation (ca. 1 mm) | 3 |
| | Serious edema with bosselation (> ca. 1 mm) | 4 |
| | Evaluation of skin irritativeness | Total of (1) and (2) |
| | Mild | ≦2 |
| | Moderate | 2-5 |
| | Serious | ≧5 |

(iii) Results

Table 5 shows the results of a primary skin irritativeness test on the samples shown in the column of Test Example 9 in Table 3 (namely, samples j, k, O and P).

TABLE 5

| Sample No. | Primary skin irritation index |
|---|---|
| j | 3.5 |
| k | 3.5 |
| O | 3.5 |
| P | 1.4 |

As Table 5 clearly shows the sample P, which contained ethyl linoleate as an unsaturated fatty acid monohydric alcohol ester, showed an extremely reduced skin irritativeness, compared with the samples j, k and O.

Table 6 shows the results of a primary skin irritativeness test on the samples shown in the column of Test Example 10 in Table 3 (namely, samples Q, R, S and T).

TABLE 6

| Sample No. | Primary skin irritation index |
|---|---|
| Q | 3.5 |
| R | 3.5 |
| S | 1.3 |
| T | 1.4 |

As Table 6 clearly shows, the samples S and T, which were respectively prepared by adding methyl linoleate and ethyl linoleate to the samples Q and R, each showed an extremely reduced skin irritativeness, compared with the samples Q and R.

Table 7 shows the results of a primary skin irritativeness test on the samples shown in the column of Test Example 11 in Table 3 (namely, samples U, V, W and X).

TABLE 7

| Sample No. | Primary skin irritation index |
|---|---|
| U | 3.5 |
| V | 3.5 |
| W | 2.5 |
| X | 2.0 |

As Table 7 clearly shows, the samples W and X, which were respectively prepared by adding ethyl oleate and methyl oleate to the samples U and V, each showed an extremely reduced skin irritativeness, compared with the samples U and V.

To further illustrate the present invention, and not by way of limitation, the following Synthetic Examples and Examples will be given.

SYNTHETIC EXAMPLE 1

(1) Synthesis of N-carbobenzoxydopamine 38.2 g (100 mmol) of sodium borate and 18.9 g (100 mmol) of dopamine hydrochloride were dissolved in 250 ml of water. To the solution thus obtained, was added a 2 N sodium hydroxide solution under a nitrogen gas stream to adjust the pH value to 9. Then 17.1 g (100 mmol) of benzyloxycarbonyl chloride was added dropwise thereto while stirring at 15° C. for 4 hours.

Simultaneously, a 2 N sodium hydroxide solution was added to maintain the pH value of the reaction mixture to 9. After continuing the stirring for 2 hours, the mixture was adjusted to pH 1 to 2 with hydrochloric acid and then extracted with diethyl ether. Next, it was dried over anhydrous magnesium sulfate and the solvent was distilled off. After washing the residue with petroleum ether, the crude crystals thus obtained were recrystallized from ethanol/n-hexane (1 : 1 by volume). Thus 27.6 g (yield: 96.5% of the desired compound (m.p.: 134°-135 ° C.) was obtained in the form of white crystals.

$^1$H-NMR (solvent: CD$_3$OD, internal standard: TMS):
δppm: 2.63 (2H, t, J=6.2 Hz, PhCH$_2$), 3.28 (2H, t, J=7.2 Hz, CH$_2$N), 5.06 (2H, s, OCH$_2$Ph), 6.50 (1H, m, ( Ar), 6.68 (2H, m, Ar) and 7.31 (5H, m, Ar).

(2) Synthesis of
3,4-di-O-pivaloyl-N-carbobenzoxydopamine

To 150 ml of a pyridine solution containing 23.0 g (98 mmol) of N-carbobenzoxydopamine obtained in Synthetic Example 1-(1), was added 24.1 g (200 mmol) of pivaloyl chloride dropwise at 5° to 10° C. After stirring at room temperature for 12 hours, the mixture was allowed to react at 35° to 40° C. for 3 hours. Further, the reaction mixture was poured into ice and a sodium carbonate solution and the stirring was continued at room temperature for 30 minutes. After extracting with diethyl ether and drying over anhydrous magnesium sulfate, the solvent was distilled off to give crude crystals. The resulting crude crystals then recrystallized from petroleum ether to obtain 27.1 g (yield: 80.1%) of the desired compound in the form of white crystals (m.p. 50°-51° C.).

$^1$H-NMR (solvent: CDCl$_3$, internal standard: TMS):
δppm: 1.32 (18H, s, CH$_3$), 2.79 (2H, t, J=6.8 Hz, PhCH$_2$), 3.42 (2H, t, J=6.6 Hz, CH$_2$N), 5.10 (2H, s, OCH$_2$Ph), 6.95 (1H, s, Ar), 7.03 (2H, s, Ar) and 7.34 (5H, m, Ar).

(3) Synthesis of 3,4-di-O-pivaloyldopamine hydrochloride 5.0 g (11 mmol) of the 3,4-di-O -pivaloyl -N-carbobenzoxydopamine obtained in Synthetic Example 1-(2) was dissolved in 50 ml of methanol and subjected to catalytic reduction under atmospheric pressure in the presence of palladium carbon for 6 hours. After filtering off the catalyst, a hydrogen chloride gas was bubbled thereto under ice-cooling for 10 minutes. Then the solvent was distilled off under reduced pressure to obtain 3.7 g (yield: 94.1%) of the desired compound in the form of hygroscopic crystals.

$^1$H-NMR (solvent: CDCl$_3$, internal standard: TMS):
δppm: 1.33 (18H, s, CH$_3$), 2.99 (2H, m, PhCH$_2$), 3.20 (2H, m, CH$_2$N) and 7.13-7.24 (3H, m, Ar).

SYNTHETIC EXAMPLE 2

(1) Synthesis of 3,4-di-O-isobutyryl-N-carbobenzoxydopamine

To 80 ml of a pyridine solution containing 10.7 g (37 mmol) of N-carbobenzoxydopamine obtained in Synthetic Example 1-(1) was added dropwise 9.9 g (93 mmol) of isobutyryl chloride at 5° to 10° C. After stirring at room temperature for 12 hours, the mixture was allowed to react at 35° to 40° C. for 3 hours. Then, the reaction mixture was poured into ice and a sodium carbonate solution and stirred at room temperature for 30 minutes. The mixture was extracted with diethyl ether and the resulting extract was dried over anhydrous magnesium sulfate. The solvent was distilled and the thus-obtained crude crystals were recrystallized from diisopropyl ether/petroleum ether (1:2 by volume) to obtain 11.9 g (yield: 74.7%) of the desired compound in the form of white cyrstals (m.p. 44°-46° C.).

$^1$H-NMR (solvent: CDCl$_3$, internal standard: TMS):
δppm: 1.29 (12H, d, J=7.0 Hz, CH$_3$), 2.77 (2H, m, >CH), 2.81 (2H, broad, s, PhCH$_2$), 3.43 (2H, m, CH$_2$N), 5.10 (2H, s, OCH$_2$Ph), 6.99-7.09 (3H, m, Ar), 7.34 (5H, m, Ar).

(2) Synthesis of 3,4-di-O-isobutyryldopamine hydrochloride 7.0 g (16.4 mmol) of 3,4-di-O -isobutyryl -N-carbobenzoxydopamine obtained in Synthetic Example 2-(1) was dissolved in 50 ml of methanol and the mixture was subjected to catalytic reduction under atmospheric pressure in the presence of palladium carbon for 6 hours. After filtering the catalyst off, a hydrogen chloride gas was bubbled thereto under ice-cooling for 10 minutes. The solvent was distilled under reduced pressure to obtain 4.4. g (yield: 81.4%) of the desired compound int he form of hygroscopic crystals.

$^1$H-NMR (solent: CDCl$_3$, internal standard: TMS):
δppm: 1.28 (12H, d, J=7.0 Hz, CH$_3$), 2.75 (2H, m, >CH), 2.92 (2H, m, PhCH$_2$), 3.15 (2H, m, CH$_2$N), 7.00-7.09 (3H, m, Ar).

SYNTHETIC EXAMPLE 3

Synthesis of 3,4-di-O-isobutyrylepinine hydrochloride 14.0 g (57 mmol) of epinine hydrobromide and 21.4 g (0.2 mol) of isobutyryl hydrochloride were added to 50 ml of 1,4-dioxane containing anhydrous hydrogen chloride in a concentration of 10%. The mixture was allowed to react at 70° C. for 12 hours and then the reaction mixture was concentrated under reduced pressure. The thus-obtained residue was dissolved in a 10% aqueous solution of sodium hydrogencarbonate so as to make the pH value 8. Then, it was extracted with chloroform and the resulting extract was dried over anhydrous magnesium sulfate. After removing the anhydrous magnesium sulfate by filtration, a hydrogen chloride gas was bubbled into the filtrate under ice-cooling. The solvent was distilled to obtain crude crystals. The thus-obtained crystals were recrystallized from ethyl acetate to obtain 17.8 g (yield: 91.7%) of the desired compound in the form of while crystals (m.p. 127°-128° C.).

$^1$H-NMR (solvent: CDCl$_3$, internal standard: TMS):
δppm: 1.29 (12H, d, J=7.0 Hz, CH$_3$), 2.69 (3H, t, J=5.4 Hz, NCH$_3$), 2.76 (2H, m, >CH), 3.17-3.25 (4H, m, PhCH$_2$CH$_2$N), 7.09-7.15 (3H, m, Ar).

SYNTHETIC EXAMPLE 4

(1) Synthesis of 3,4-di-O-nicotinoyl-N -carbobenzoxydopamine 19.0 g (66 mmol) of N-carbobenzoxydopamine obtained in Synthetic Example 1-(1) and 37.2 g (209 mmol) of hydrochloride of nicotinoyl chloride were added to 200 ml of pyridine. After stirring at room temperature for 12 hours, the mixture was allowed to react at 35°-40° C. for 2 hours. Then, the reaction mixture was poured into ice and a sodium carbonate solution followed by extraction with chloroform. The resulting extract was dried over anhydrous magnesium sulfate and the solvent was distilled off to obtain crude crystals. The thus-obtained crystals were recrystallized from ethyl acetate/diethyl ether (1:5 by volume) to obtain 23.5 g (yield: 71.6%) of the desired compound in the form of white crystals (m.p. 77°–78° C.).

$^1$H-NMR (solvent: CDCl$_3$, internal standard: TMS): δppm: 2.90 (2H, m, PhCH$_2$), 3.50 (2H, m, CH$_2$N), 5.11 (2H, s, OCH$_2$Ph), 7.23–7.37 (10H, m, Ar), 8.29 (2H, m, Ar), 8.77 (2H, m, Ar), 9.24 (2H, d, J=1.9 Hz, Ar)

(2) Synthesis of 3,4-di-O-nicotinoyldopamine hydrochloride 10.0 g (20 mmol) of 3,4-di-O -nicotinoyl -N-carbobenzoxydopamine obtained in Synthetic Example 4-(1) was added to 200 ml of trifluoroacetic acid and heated under reflux for 1 hour. After distilling the solvent under reduced pressure, the residue was dissolved in 1,4-dioxane and a hydrogen chloride gas was bubbled thereto under ice-cooling. Then, the solvent was distilled under reduced pressure and the thus-obtained crude crystals were recrystallized from methanol/ethyl acetate (1:3 by volume) to obtain 4.4 g (yield: 46%) of the desired compound in the form of white crystals (m.p. 169°–172° C.).

$^1$H-NMR (solvent: CD$_3$OD, internal standard: TMS): δppm: 3.12 (2H, m, PhCH$_2$), 3.29 (2H, m, CH$_2$N), 7.45–7.60 (3H, m, Ar), 8.23 (2H, m, Ar), 9.11 (2H, m, Ar), 9.17 (2H, m, Ar), 9.51 (2H, m, Ar)

EXAMPLE 1

Oily ointment

An oily ointment having the following composition was prepared as described below.

Cetyl lactate was heated to 60° C. and 3,4-di-O-isobutyryldopamine hydrochloride ahd ethylenediamin tetraacetic acid disodium salt were added thereto. The resulting mixture was homogenized by stirring. Separately, sorbitan oleate, white vaseline and ethyl linoleate were heated to 60° C. and homogeneously mixed together, and to this mixture was added the above-obtained mixture. The whole mixture was then thoroughly stirred and cooled to room temperature to give a desired oily ointment.

|  | [% by weight] |
| --- | --- |
| 3,4-di-O-isobutyryldopamine hydrochloride | 5.0 |
| ethylenediamine tetraacetic acid disodium salt | 0.5 |
| cetyl lactate | 3.0 |
| sorbitan oleate | 3.0 |
| white vaseline | 86.5 |
| ethyl linoleate | 2.0 |

EXAMPLE 2

Hydrophilic ointment

A hydrophilic ointment having the following composition was prepared as described below.

Myristyl lactate, ethylenediaminetetraacetic acid disodium salt, polyoxyethylene (20) sorbin monooleate, official macrogol ointment (J. P.) and ethyl benzoate as a preservative were heated to 60° C. and homogeneously mixed together. Then a fine powder of 3,4-di-O-isobutyryldopamine hydrochloride and methyl linoleate were added thereto. The obtained mixture was thoroughly mingled under cooling to give a desired hydrophilic ointment.

|  | [% by weight] |
| --- | --- |
| 3,4-di-O-isobutyryldopamine hydrochloride | 5.0 |
| myristyl lactate | 5.0 |
| ethylenediamine tetraacetic acid disodium salt | 0.5 |
| polyoxyethylene (20) sorbitan monooleate | 2.0 |
| macrogol ointment (JP) | 82.4 |
| ethyl benzoate | 0.1 |
| methyl linoleate | 5.0 |

EXAMPLE 3

O/W type cream

An O/W type cream having the following composition was prepared as described below.

Squalane, isopropyl myristate, stearic acid, stearic acid monoglyceride, sorbitan monopalmitate, polyoxyethylene (20) sorbitan monostearate, myristyl lactate and ethylenediamine tetraacetic acid disodium slat were heated to 70° C. and homogeneously molten together. Then 3,4-di-O-isobutyrylepinine hydrochloride was added thereto and the obtained mixture was homogenized by stirring. Separately, propylene glycol, bezoic acid as an antiseptic and purified water were heated to 60° c. and then slowly added thereto. The mixture was cooled to approxiamtely 30° C. under stirring. Thus a desired O/W type cream was obtained.

|  | [% by weight] |
| --- | --- |
| 3,4-di-O-isobutyrylepinine hydrochloride | 5.0 |
| myristyl lactate | 5.0 |
| squalane | 8.0 |
| isopropyl myristate | 4.0 |
| stearic acid | 4.0 |
| stearic acid monoglyceride | 4.0 |
| sorbitan monopalmitate | 1.5 |
| polyoxyethylene (20) sorbitan monostearate | 1.5 |
| ethylenediaminetetraacetic acid disodium salt | 0.5 |
| propylene glycol | 5.0 |
| benzoic acid | 0.1 |
| purified water | 61.4 |

EXAMPLE 4

Oily ointment

An oily ointment having the following compositons was prepared as described below.

Cetyl lactate and lauryl lactate were heated to 55° C. and ethylenediaminetetraacetic acid disodium salt and 3,4-di-O -isobutyrylepinine hydrochloride were added thereto. The obtained mixture was homogenized. Separately, the another mixture was prepared by heating octyldodecyl myristate, sorbitan sesqui-oleate, purified lanolin, propylene glycol monostearate and white vaseline to 70° C. and homogenizing them. The former mixture was added to the latter one and the resulting mixture was cooled under stirring to give an oily ointment.

|  | [% by weight] |
| --- | --- |
| 3,4-di-O-isobutyrylepinine hydrochloride | 5.0 |
| cetyl lactate | 3.0 |
| lauryl lactate | 3.0 |
| octyldodecyl myristate | 10.0 |
| sorbitan sesqui-oleate | 5.0 |
| purified lanolin | 10.0 |
| propylene glycol monostearate | 2.0 |
| ethylenediaminetetraacetic acid disodium salt | 0.5 |

| -continued | [% by weight] |
|---|---|
| white vaseline | 61.5 |

EXAMPLE 5
Oily ointment base

An oily ointment base having the following composition was prepared as described below.

Propylene glycol was heated to 60° C. and 3,4-di-O-nicotinoyldopamine hydrochloride and ethylenediaminetetraacetic acid disodium salt were added thereto. These were mixed by stirring. Then a mixture of cetyl lactate and PLASTIBASE (registered trade name of the product manufactured by E. R. Squib & Sons, Inc.; comprising 95% by weight of liquid paraffin and 5% by weight of polyethylene having a molecular weight of 10,000 to 30,000), which had been preliminarily heated to 60° C. and mixed, was added thereto. The resulting mixture was cooled to room temperature under stirring to give a desired oily ointment base.

| | [% by weight] |
|---|---|
| 3,4-di-O-nicotinoyldopamine hydrochloride | 5.0 |
| cetyl lactate | 10.0 |
| propylene glycol | 15.0 |
| ethylenediaminetetraacetic acid disodium salt | 0.5 |
| Plastibase | 69.5 |

EXAMPLE 6
Plaster

A plaster having the following composition was prepared as described above.

SIS rubber (manufactured by Shell Chemical Co.), ARKON P-100 (registered trade name of the product manufactured by Arakawa Kagaku Kogyo K. K., alicyclic petroleum resin) and liquid paraffin, which had been molten at 130° C., were mixed with cetyl lactate, glycerol monooleate and dibutylhydroxytoluene, which had been molten at 70° C., and the mixture was cooled to 60° C. under stirring. Next, 3,4-di-O-isobutyryldopamine hydrochloride and ethylenediaminetetraacetic acid disodium salt were added thereto and the resulting mixture was homogenized by stirring. Then it was spreaded onto laminated films of polyethylene terephthalate to give a desired plaster.

| | [% by weight] |
|---|---|
| SIS rubber | 35.0 |
| Arcon P-100 | 24.0 |
| liquid paraffin | 24.5 |
| 3,4-di-O-isobutyryldopamine hydrochloride | 5.0 |
| cetyl lactate | 5.0 |
| glycerol monooleate | 5.0 |
| dibutylhydroxytoluene | 1.0 |
| ethylenediaminetetraacetic acid disodium salt | 0.5 |

EXAMPLE 7
Plaster

A plaster having the following composition was prepared as desired below.

SIS rubber (manufactured by Shell Chemical Co.), Arcon P-100 (trade name of the product manufactured by Arakawa Kogyo K. K., alicyclic petroleum resin) and liquid paraffin, which had been molten at 130° C., were mixed with lauryl alcohol and dibutylhydroxytoluene, which had been molten at 70° C., and the mixture was cooled to 60° C. under stirring. Next, 3,4-di-O-pivaloyldopamine hydrochloride, methyl linoleate and ethylenediaminetetraacetic acid disodium salt were added thereto and the resulting mixture was homogenized by stirring. Then it was spreaded onto laminated films of polyethylene vinyl alcohol to give a desired plaster.

| | [% by weight] |
|---|---|
| SIS rubber | 35.0 |
| Arcon P-100 | 24.0 |
| liquid paraffin | 24.5 |
| 3,4-di-O-pivaloyldopamine hydrochloride | 5.0 |
| lauryl alcohol | 5.0 |
| methyl linoleate | 5.0 |
| dibutylhydroxytoluene | 1.0 |
| ethylenediaminetetraacetic acid disodium salt | 0.5 |

While the invention has been described in detail and with reference to specific embodiments thereof, it will be apparent to one skilled in the art that various changes and modifications can be made therein without departing from the spirit and scope thereof.

What is claimed is:

1. A preparation for endermism which comprises:
(A) a diacylated dopamine derivative represented by the formula (I)

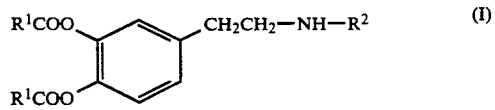

wherein $R^1$ represents an alkyl group having 3 to 7 carbon atoms, a cycloalkyl group having 3 to 6 carbon atoms, a phenyl group, a phenyl group substituted with a methyl group or a methoxy group, a pyrrolyl group, a pyrazolyl group, a pyridyl group, a pyridyl group substituted with bromine or a methyl group, or a pyrazinyl group; and $R^2$ represents a hydrogen atom or a lower alkyl group; or a salt thereof, in an amount effective to treat hypotension or cardiac circulatory insufficiency and (b) one or more compounds selected from lactic acid esters, in an amount effective to promote the percutaneous absorption of said dopamine derivative or a salt thereof.

2. A preparation for endermism as claimed in claim 1, wherein $R^1$ is a branched alkyl group.

3. A preparation for endermism as claimed in claim 1, wherein $R^1$ is a pyridyl group.

4. A preparation for endermism as claimed in claim 1, wherein said lactic acid ester is selected from myristyl lactate, cetyl lactate and lauryl lactate.

5. A preparation for endermism as claimed in claim 1, wherein said diacylated dopamine derivative or a salt thereof is contained in an amount of 1 to 20% by weight based on the weight of the preparation.

6. A preparation for endermism as claimed in claim 1, wherein said ingredient (B) is contained in a proportion of 0.1 to 5 by weight to the dopamine derivative or a salt thereof.

7. A preparation for endermism as claimed in claim 1, wherein said ingredient (B) is contained in a proportion of 0.5 to 3 by weight to the dopamine derivative or a salt thereof.

* * * * *